United States Patent [19]

Kathawala

[11] B 3,997,567

[45] Dec. 14, 1976

[54] SUBSTITUTED 2-(4-PHENOXYPHENYL)-2-TERTIARY BUTYL-1,3-DIOXALANES

[75] Inventor: Faizulla G. Kathawala, West Orange, N.J.

[73] Assignee: Sandoz, Inc., E. Hanover, N.J.

[22] Filed: Nov. 7, 1974

[21] Appl. No.: 521,643

[44] Published under the second Trial Voluntary Protest Program on March 2, 1976 as document No. B 521,643.

[52] U.S. Cl. .......................... 260/340.9; 260/592; 424/278

[51] Int. Cl.[2] ....................................... C07D 317/22

[58] Field of Search ............................. 260/340.9

[56] References Cited

FOREIGN PATENTS OR APPLICATIONS 1,080,536   4/1960   Germany

Primary Examiner—Richard L. Raymond
Attorney, Agent, or Firm—Gerald D. Sharkin; Richard E. Vila; Joseph J. Borovian

[57] ABSTRACT

Hypolipidemic agents of the formula:

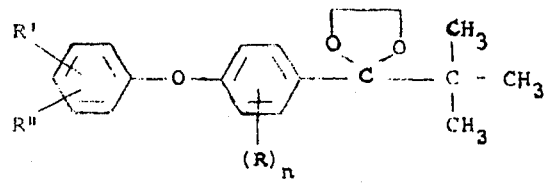

wherein
R is hydrogen, alkyl or halo,
R' and R'' are hydrogen, halo, alkyl or alkoxy, and
n is 1 or 2.

4 Claims, No Drawings

SUBSTITUTED 2-(4-PHENOXYPHENYL)-2-TERTIARY BUTYL-1,3-DIOXALANES

The present invention relates to substituted 2-(4-phenoxyphenyl)-2-tertiary butyl-1,3-dioxalanes and to their use as hypolipidemics. The invention also relates to pharmaceutical compositions containing the above compounds as an active ingredient thereof and to the method of using such compositions for the treatment of lipidemia.

The compounds with which this invention is concerned may be represented by the following structural formula:

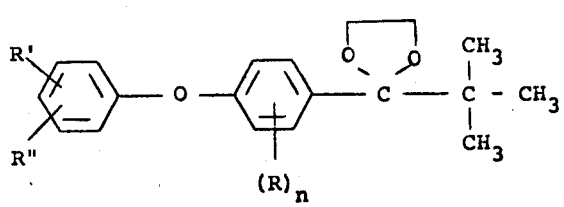

(I)

wherein

R is hydrogen, alkyl of 1 to 4 carbon atoms, or halo of atomic weight of from 18 to 36, R' and R" are independently hydrogen, halo of atomic weight of from 18 to 36, alkyl of 1 to 4 carbon atoms or alkoxy of 1 to 4 carbon atoms, and n is 1 or 2.

The compounds of formula (I) may be prepared by the following reaction scheme:

wherein R, R', R" and n are as defined above. This process is conducted by reacting (II) with ethylene glycol in the presence of an aromatic sulfonic acid and an inert, organic, aromatic solvent at temperatures in the range of 80° to 140°C., preferably at the reflux temperature of the system, for a period of time between 12 and 36 hours. Although the particular aromatic sulfonic acid employed is not critical, p-toluene sulfonic acid is preferred. The reaction is carried out in the presence of an inert, organic, aromatic solvent such as benzene, xylene and toluene, the latter being particularly preferred.

The compounds of formula (II) may be prepared by reacting a compound of the formula (III):

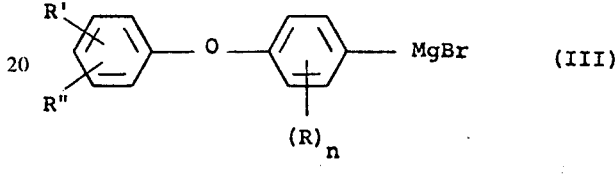

(III)

in which R, R', R" and n are as defined, with a compound of the formula (IV):

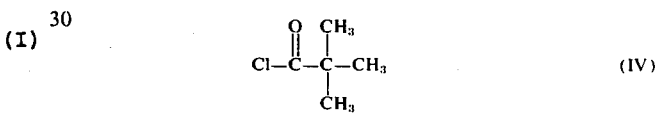

(IV)

and hydrolyzing the resulting product.

The reaction may be carried out at temperatures in the range of from 0° to 100°C. The reaction is conveniently carried out in the presence of an inert organic solvent of conventional type including the cyclic and acyclic ethers, such as diethyl ether and tetrahydrofuran.

The hydrolysis may be effected under alkaline, neutral or acid conditions, preferably mild acidic conditions, suitably using hydrochloric or sulfuric acid, pref-

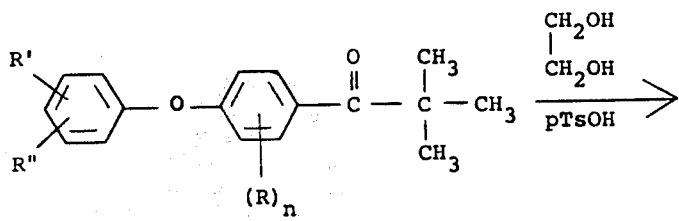

(II)

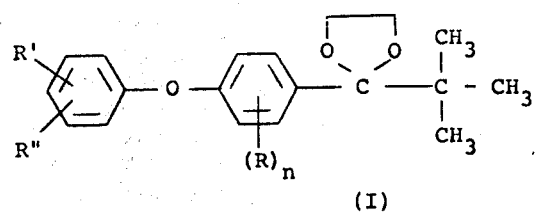

(I)

erably hydrochloric acid. The hydrolysis may be carried out conveniently at a temperature of from −40° to 100°C., preferably at a temperature of from 10° to 30°C.

The compounds of formula (III) may be prepared by reacting a compound of the formula (V):

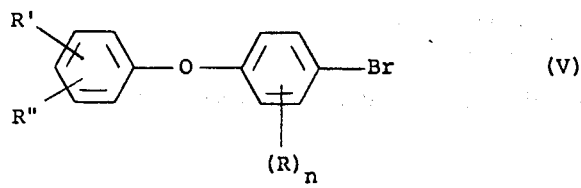

in which R, R', R" and $n$ are as defined, with magnesium in a conventional manner for preparation of a Grignard compound from the corresponding bromo compound.

Certain of the compounds of the formula (V) are known and may be prepared by methods disclosed in the literature. Those compounds not specifically disclosed may be prepared by analagous methods from known starting materials.

The compounds of formula (I) may be recovered using conventional techniques such as crystallization, filtration or column chromatography.

As previously indicated, the compounds of formula (I) are useful because they possess pharmacological activity in animals, e.g., mammals. In particular, the compounds of formula (I) are useful as hypolipidemic agents in the treatment of lipidemia, in particular, hyperlipoproteinemia as indicated by the fall in cholesterol and/or triglyceride levels in malo albino Wistar rats weighing 110–130 g. initially. The rats are maintained on drug-free laboratory chow diet for seven days and then divided into groups of 8 to 10 animals. Each group with the exception of the control is then given the compound orally at a dose of 7.5, 30, 250, or 500 milligrams per kilogram of body weight per day, p.o. for 6 days. At the end of this period, the animals are anesthetized with sodium hexobarbital and bled from the carotid arteries. Serum or plasma samples are then extracted with isopropanol, and the cholesterol content of the extracts is estimated on a Technicon Autoanalyzer by standard methodology. For example, 1.0 ml. of serum is added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345–347) are added; and the mixture is shaken for 1 hour. Cholesterol levels are determined using this sample by the standard Technicon N 24A (cholesterol) methodology. The mean total serum cholesterol levels are then computed and the hydrocholesterolemic activity is expressed as the fall in cholesterol levels as a percentage of the control level. For the triglyceride determination, blood samples are collected as above and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345–347) are added; and the mixture is shaken for 1 hour. After centrifugation, 2 ml. of the clear supernates are evaporated to dryness and saponified by addition of 0.1 ml. 10% KOH in 90% ethanol and 1.0 ml. Skelly B (petroleum ether b.p. 60°–70°C.). After acidification and the removal of fatty acids with petroleum ether, the aqueous phases are neutralized, suitably diluted with water, and analyzed for glycerol by the method of Lofland (Anal. Biochem. 9, 393, 1964) using the Technicon Autoanalyzer. The change in serum triglyceride levels induced by the drug is computed as a percentage of the control triglyceride levels.

For such usage, the compounds may be administered orally or parenterally, preferably orally, and in admixture with conventional pharmaceutical carriers. The anti-hyperlipidemic effective dosage of the compounds of formula I employed for the alleviation of lipidemia may vary depending on the particular compound employed and the severity of the condition being treated. In general, satisfactory results are obtained when administered at a daily dosage of from about 4 milligrams to about 250 milligrams per kilogram of animal body weight, preferably given orally and in divided doses, 2 to 4 times a day, or in sustained release form. For most mammals, the total daily dosage is from about 300 milligrams to about 3000 milligrams of the compound, and dosage forms suitable for internal administration comprise from about 75 to 1500 milligrams of the compound in admixture with a solid or liquid pharmaceutically acceptable carrier or diluent.

For above usage, the compounds of formula I may be administered orally in such forms as tablets, dispersible powders, granules, capsules, syrups and elixirs; and parenterally as solutions, suspensions, dispersions, emulsions, and the like, e.g., a sterile injectable solution such as an aqueous suspension. These pharmaceutical preparations may contain 0.5% up to about 90% of the active ingredient in combination with the carrier or adjuvant, more usually between 3% and 50% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate).

Capsules may contain the active ingredient alone or admixed with an inert liquid or solid diluent, e.g., calcium carbonate, calcium phosphate, kaolin, peanut oil, sesame oil and corn oil. The preferred pharmaceutical compositions from the standpoint of preparation and ease of administration are solid compositions, particularly hard-filled capsules and tablets.

Capsules containing the ingredients indicated below may be prepared by conventional techniques and are useful in treating lipidemia, particularly hyperlipoproteinemia, in mammals at a dose of one capsule, 2 to 4 times a day.

| Ingredients | Weight (mg.) |
| --- | --- |
| 2-(4-phenoxyphenol)-2-tertiary butyl-1,3-dioxalane | 150 |
| kaolin | 200 |
| Total | 350 mg. |

The following examples are merely illustrative of specific compounds of the invention and the manner in which they may be prepared.

EXAMPLE 1

2-(4-phenoxyphenyl)-2-tertiary butyl-1,3-dioxalane

A mixture of 12.7 g. of 4-phenoxy-pivalophenone, 50 ml. of ethylene glycol and 1 g. of p-toluenesulfonic acid. in 200 ml. of toluene is refluxed for 14 hours using a Dean-Stark trap to remove water formed in the reaction. The resultant toluene solution is extracted several times with a 10% sodium bicarbonate solution, washed with water, dried over potassium carbonate, filtered, evaporated in vacuo to dryness and the residue recrystallized from pentane to obtain 2-(4-phenoxyphenyl)-2-tertiary butyl-1,3-dioxalane, m.p. 66°-67°C.

EXAMPLE 2

Following essentially the procedure of Example 1, and using in place of 4-phenoxy-pivalophenone, an equivalent amount of:
a) 4-(p-methoxyphenoxy)-pivalophenone,
b) 4-(m-chlorophenoxy)-pivalophenone,
c) 4-(p-methoxyphenoxy)-3,5-dichloro-pivalophenone,
d) 4-(p-methoxyphenoxy)-3-chloro-pivalophenone,
e) 4-phenoxy-3-methyl-pivalophenone,
f) 4-(p-methylphenoxy)-pivalophenone,
g) 4-(m-chloro-p-methoxyphenoxy)-3,5-dichloro-pivalophenone,
h) 4-(3',5'-di-t-butylphenoxy)-pivalophenone,
i) 4-(p-chlorophenoxy)-pivalophenone, and
j) 4-phenoxy-3,5-dichloro-pivalophenone,
there is obtained
a) 2-[4-(p-methoxyphenoxy)phenyl]-2-t-butyl-1,3-dioxalane, m.p. 47°-49°C.,
b) 2-[4-(m-chlorophenoxy)phenyl]-2-t-butyl-1,3-dioxalane,
c) 2-[4-(p-methoxyphenoxy)-3,5-dichlorophenyl]-2-t-butyl-1,3-dioxalane,
d) 2-[4-(p-methoxyphenoxy)-3-chlorophenyl]-2-t-butyl-1,3-dioxalane,
e) 2-(4-phenoxy-3-methylphenyl)-2-t-butyl-1,3-dioxalane,
f) 2-[4-(p-methylphenoxy)phenyl]-2-t-butyl-1,3-dioxalane,
g) 2-[4(m-chloro-p-methoxyphenoxy)-3,5-dichlorophenyl]-2-t-butyl-1,3-dioxalane,
h) 2-[4-(3',5'-di-t-butylphenoxy)phenyl]-2-t-butyl-1,3-dioxalane,
i) 2-[4-(p-chlorophenoxy)phenyl]-2-t-butyl-1,3-dioxalane, and
j) 2-(4-phenoxy-3,5-dichlorophenyl)-2-t-butyl-1,3-dioxalane, respectively.

EXAMPLE 3

Preparation of 4-phenoxy-pivalophenone

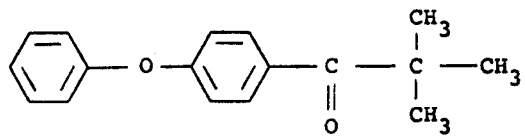

To a flask containing 33.6 g. of magnesium and crystals of iodine, is added 50–70 ml. of a solution of 300 g. of (p-bromophenyl)phenyl ether in 500 ml. of tetrahydrofuran. The remainder of the solution is added as needed to maintain a gentle reflux and the resulting mixture heated to reflux for 30 minutes. The resulting mixture is then added to a solution of trimethylacetyl chloride in 500 ml. of tetrahydrofuran at a rate to maintain 40°–50°C. The resulting mixture is then stirred at ambient temperature for one hour and then 200 ml. of 2N. hydrochloric acid is added. The organic layer is washed twice with one liter of 2N. sodium carbonate solution, dried and evaporated in vacuo to a liquid weighing about 290 g. This liquid is distilled under reduced pressure to obtain 4phenoxy-pivalophenone, b.p. 136°–139°C. at 0.1 mm/Hg.

What is claimed is:
1. A compound of the formula:

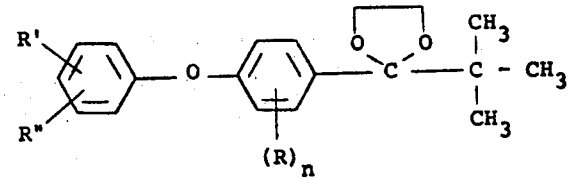

wherein
R is hydrogen, alkyl of 1 to 4 carbon atoms, or halo of atomic weight of from 18 to 36,
R' and R" are independently hydrogen, halo of atomic weight of from 18 to 36, alkyl of 1 to 4 carbon atoms or alkoxy of 1 to 4 carbon atoms, and
n is 1 or 2.
2. A compound of claim 1 having the formula:

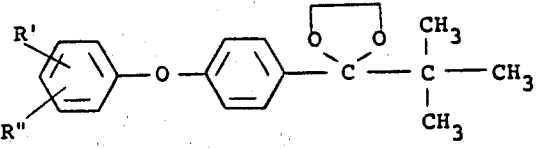

wherein R' and R" are as defined in claim 1.
3. A compound of claim 2 which is 2-[4-(p-methoxyphenoxy)phenyl]-2-t-butyl-1,3-dioxalane.
4. A compound of claim 2 which is 2-(4-phenoxyphenyl)-2-*t*-butyl-1,3-dioxalane.